US00PP24726P3

(12) United States Plant Patent
Bédard

(10) Patent No.: US PP24,726 P3
(45) Date of Patent: Aug. 5, 2014

(54) FLORIBUNDA ROSE PLANT NAMED 'WEKJUNJUC'

(50) Latin Name: *Rosa hybrida*
Varietal Denomination: WEKjunjuc

(71) Applicant: Early Morning LLC, Pomona, CA (US)

(72) Inventor: Christian Bédard, Brea, CA (US)

(73) Assignee: Early Morning LLC, Pomona, CA (US)

( * ) Notice: Subject to any disclaimer, the term of this patent is extended or adjusted under 35 U.S.C. 154(b) by 116 days.

(21) Appl. No.: 13/694,323

(22) Filed: Nov. 19, 2012

(65) Prior Publication Data

US 2014/0143917 P1 May 22, 2014

(51) Int. Cl.
*A01H 5/00* (2006.01)

(52) U.S. Cl.
USPC ..... Plt./145; Plt./141

(58) Field of Classification Search
USPC ..... Plt./145, 141
See application file for complete search history.

(56) References Cited

U.S. PATENT DOCUMENTS

PP17,175 P2 10/2006 Carruth
PP18,473 P2 2/2008 Carruth

*Primary Examiner* — Susan McCormick Ewoldt
(74) *Attorney, Agent, or Firm* — McKee, Voorhees & Sease, P.L.C.

(57) ABSTRACT

A new variety of Floribunda rose suitable for garden decoration, having flowers of sparkling clear yellow coloration.

1 Drawing Sheet

Classification: The present invention relates to a new *Rosa hybrida* plant.

Variety denomination: The new plant has the varietal denomination 'WEKjunjuc'.

BACKGROUND OF THE INVENTION

This invention relates to a new and distinct variety of Floribunda Rose. It has as its seed parent the variety known as 'WEKlezpat' (U.S. Plant Pat. No. 17,175) and as its pollen parent the variety known as 'WEKvossutono' (U.S. Plant Pat. No. 18,473).

SUMMARY OF THE INVENTION

Among the features which distinguish the new variety from other presently available and commercial rose cultivars known to the inventor are the following combinations of characteristics: its moderate licorice to apple-like fragrance, its excellent color stability throughout the life of the flower and its large flower size for the class. The plant has a bushy rounded growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKjunjuc' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKlezpat' by the following combination of characteristics: whereas 'WEKjunjuc' bears double flowers (about 30 to 41 petals) of sparkling clear yellow coloration, 'WEKlezpat' bears very double flowers of butter gold blushed pink coloration with significantly heavier petalage (about 48 to 72 petals). The new variety is classified as a Floribunda rose with a bushy rounded medium height growing habit (about 120 to about 150 cm. in height), whereas the seed parent is classified as a Hybrid Tea rose with an upright moderately spreading significantly taller growing habit (about 152 to about 170 cm. in height).

The new variety may be distinguished from its pollen parent, 'WEKvossutono' by the following combination of characteristics: whereas 'WEKjunjuc' bears flowers of sparkling clear yellow coloration with a moderate licorice to apple-like fragrance, 'WEKvossutono' bears flowers of butter gold coloration with a stronger licorice fragrance. The new variety has a bushy rounded medium height growing habit (about 120 to about 150 cm. in height and about 170 to about 200 cm. spread at the widest point), whereas the pollen parent has a compact and bushy significantly shorter and more compact growing habit (about 70 to about 85 cm. in height and about 50 to about 65 cm. spread at the widest point).

COMPARISON WITH THE CLOSEST COMMERCIALLY AVAILABLE CULTIVAR

The closest commercially available cultivar to the new variety is the pollen parent 'WEKvossutono' (U.S. Plant Pat. No. 18,473).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety sometimes bears its flowers singly, sometimes in clusters of two to three or more per stem. Flowers may be borne in regular rounded clusters on strong medium length stems (about 26 to about 54 cm.). Outdoors, the plant blooms abundantly and nearly continuously during the growing season. The flowers have a moderate licorice to apple-like fragrance.

BUD

The peduncle is about 1.6 to about 5.2 cm. in length, of average caliper (about 0.2 to about 0.3 cm. in diameter), and usually erect. It is smooth, with few stipitate glands, and some hairs. Peduncle color is between 146C and 146B sometimes very lightly suffused, especially on the side exposed to the sun, with near 187C.

Before the calyx breaks, the bud is about 1.1 to about 1.7 cm. in diameter at the widest point, about 1.4 to about 2.3 cm. in length, and pointed in shape. The surface of the bud bears between 3 to 8 foliaceous appendages and some hairs, usually with entire foliaceous parts extending beyond the tip of the bud about ½ or more of its length. Bud color is between 146B and 146A sometimes moderately suffused, especially on the side exposed to the sun, with between 187A and 187B.

The sepals are about 2.2 to about 3.7 cm. in length and about 0.7 to about 1.1 cm. in width at the widest point. The outer surface color of the sepal is between 146B and 146A sometimes moderately suffused, especially on the side exposed to the sun, with between 187A and 187B. The outer surface of the sepal is smooth with some hairs and bears between 1 to 3 foliaceous appendages. The inner surface color of the sepal is near 138B broadly bordered by near 139A. The inner surface of the sepal is covered with fine wooly tomentum; sepal margins are lined with some stipitate glands and hairs.

The receptacle of the flower is of medium length (about 0.4 to about 0.7 cm.) and somewhat heavy in caliper (about 0.7 to about 1.2 cm. in diameter). The receptacle is urn-shaped in form. Its surface is smooth with some hairs and with thick fleshy walls. The receptacle color is between 146B and 146A.

As the petals open (after the calyx breaks), the bud is about 1.5 to about 1.8 cm. in diameter at the widest point, about 2.6 to about 3.2 cm. in length, and moderately ovoid to somewhat pointed in form. The color of the under surfaces of the newly opened petals is between 13B and 15C. There is no visible change in coloration at the point where the petal attaches. The color of the upper surfaces of the newly opened petals is between 14B and 15C. There is no visible change in coloration at the point where the petal attaches.

BLOOM

When fully open, the bloom ranges from about 6.7 to about 10.4 cm. in diameter. Petalage is double with about 30 to 41 petals and about 9 to 11 petaloids irregularly arranged. When partially open, the bloom form is somewhat ovoid to moderately cupped, and the petals are loosely spiraled to cupped to somewhat undulated with petal edges somewhat reflexed outward. When fully open, the bloom form is more cupped, and the petals are loosely cupped to moderately undulated with petal edges somewhat reflexed outward.

PETALS

The substance of the petals is somewhat heavy and of moderately thin thickness, with upper surfaces moderately satiny and under surfaces slightly shiny to matte. The petals are about 2.5 to about 5.1 cm. in length and about 2.0 to about 4.7 cm. in width at the widest point. Petal margins are entire.

The outer petals are moderately obovate to somewhat rounded in shape with rounded apices.

The inner petals are obovate in shape with rounded apices and sometimes notched with one notch.

Petaloids are about 1.6 to about 3.2 cm. in length and about 0.5 to about 2.4 cm. in width at the widest point. Petaloids are irregularly shaped somewhat oblanceolate to subulate with rounded apices.

NEWLY OPENED FLOWER

The under surface color of the outer, intermediate and inner petals is between 13C and 15C. There is no visible change in coloration at the point where the petal attaches. The upper surface color of the outer, intermediate and inner petals is between 12B and 15C. There is no visible change in coloration at the point where the petal attaches.

The under and upper surface colors of the petaloids are similar in coloration to the upper and under surfaces of the intermediate and inner petals.

The general tonality of the newly opened flower is between 12B and 15C.

THREE-DAY-OLD FLOWER

The under surface color of the outer, intermediate and inner petals is between 10A and 15C. There is no visible change in coloration at the point where the petal attaches. The upper surface color of the outer, intermediate and inner petals is between 9C and 15C. There is no visible change in coloration at the point where the petal attaches.

The under and upper surface colors of the petaloids are similar in coloration to the upper and under surfaces of the intermediate and inner petals.

The general tonality of the three-day-old flower is between 9C and 15C.

On the spent bloom, the petals usually drop off cleanly and are not particularly affected by cold, hot, wet, or dry weather.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 115) and are arranged regularly about the pistils; a few are mixed with petaloids. The filaments are of somewhat short length (about 0.4 to about 0.8 cm.) most with anthers. Filaments are between 14B and 13A in color. The anthers are of medium to somewhat large size for the class and all open approximately at the same time. Anther color when immature is near 20A on the external part and near 16D on the internal part. Anther color at maturity is near 163A on the external part and near 200A on the internal part. Pollen is abundant and between 16D and 18B in color.

FEMALE REPRODUCTIVE ORGANS

Pistils vary in number (average about 95). The styles are moderately even, average in length (about 0.4 to about 0.7 cm.), average in caliper, and loosely bunched to somewhat separated. Stigma color is between 13C and 11A. Style color is near 150C usually heavily suffused with between 53B and 53C. Ovaries are usually all enclosed in the calyx.

Hips are moderately long in length (about 2.0 to about 2.4 cm.), rounded in form with a flat top, and between 28B and 30C in color when ripe. The hip surface is smooth with thick fleshy walls. The sepals are permanent and usually straight in shape.

The seeds are irregularly rounded, smooth in texture, approximately 16 to about 22 per hip, about 0.4 to about 0.7 cm. in diameter at the widest point and between 164C and 165C in color.

FOLIAGE

The compound leaves are usually comprised of three to seven leaflets and are borne abundantly. The five-leaflet leaves are about 8.3 to about 13.4 cm. in length and about 6.0 to about 9.8 cm. in width at the widest point, moderately leathery to somewhat crisp in texture, and glossy in finish on the upper side and matte to slightly shiny in finish on the underside. The leaves have a pinnate venation pattern. The terminal leaflets are about 3.6 to about 5.6 cm. in length and about 2.6 to about 4.5 cm. in width at the widest point, shaped ovate to somewhat oval with acute apices and rounded bases. Their margins are usually simply serrate.

The upper surface color of the mature leaf is between 137A and 147A. The under surface color of the mature leaf is between 147B and 146A. The under and upper colors of the leaf veins on the mature leaf are similar in coloration to the upper and under surfaces colors of the mature leaf. The upper surface color of the young leaf is between 137A and 146A, often heavily suffused with between 187A and 187B. The under surface color of the young leaf is between 147B and 146A, often heavily suffused with between 187B and 187A. The under and upper colors of the leaf veins on the young leaf are similar in coloration to the upper and under surfaces colors of the young leaf.

The rachis is somewhat light in caliper and rough. The upper side is shallowly grooved with few hairs and some stipitate glands on the edges of the grooves. The under side of the rachis is rough with few stipitate glands and small prickles. The rachis color is near 146D on the underside and near 137C on the upper side.

The stipules are about 0.9 to about 1.9 cm. in length and somewhat wide (about 0.4 to about 0.8 cm.) with moderately long straight points that usually turn out at an angle of more than 45 degrees and sometimes recurve toward the stem. The under and upper surface color of the stipule is between 137B and 137C sometimes moderately suffused with between 187B and 187C.

The petiole is somewhat light in caliper and smooth. The upper side is shallowly grooved with few hairs and some stipitate glands on the edges of the grooves. The under side of the petiole is smooth. The petiole is about 0.9 to about 1.9 cm. in length and about 0.1 to about 0.15 cm in width at the widest point. The petiole color is near 146D on the underside and near 137C on the upper side.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has a bushy rounded medium height growing habit (about 120 to about 150 cm. in height and about 170 to about 200 cm. spread at the widest point), with full branching. It displays moderately vigorous growth and the canes are of somewhat heavy caliper for the class (about 1.8 to about 2.4 cm. in diameter at the widest point).

The color of the major stems is between 146D and 137C. They bear many large prickles that are about 0.6 to about 0.9 cm. in length. The large prickles are angled slightly downward with a medium length somewhat broad oval base; prickle color is between 165A and 165B. The major stem bears few small prickles of similar shape and coloration.

The color of the branches is between 146A and 146B. They bear some large prickles which are of similar shape to the large prickles on the major stems. The prickles are about 0.5 to about 0.6 cm. in length. The prickle color is between 147C and 148B sometimes moderately suffused with between 187B and 187C. The branches bear very few small prickles of similar shape and coloration.

The color of the new shoots is between 146B and 146A sometimes lightly suffused with between 187B and 183A. They bear some large prickles which are of similar size and shape to the large prickles on the branches; prickle color is between 147C and 148B often moderately suffused with between 187B and 187C. The shoots bear very few small prickles of similar shape and coloration.

I claim:

1. A new and distinct Floribunda rose plant of the variety substantially as described and illustrated herein.

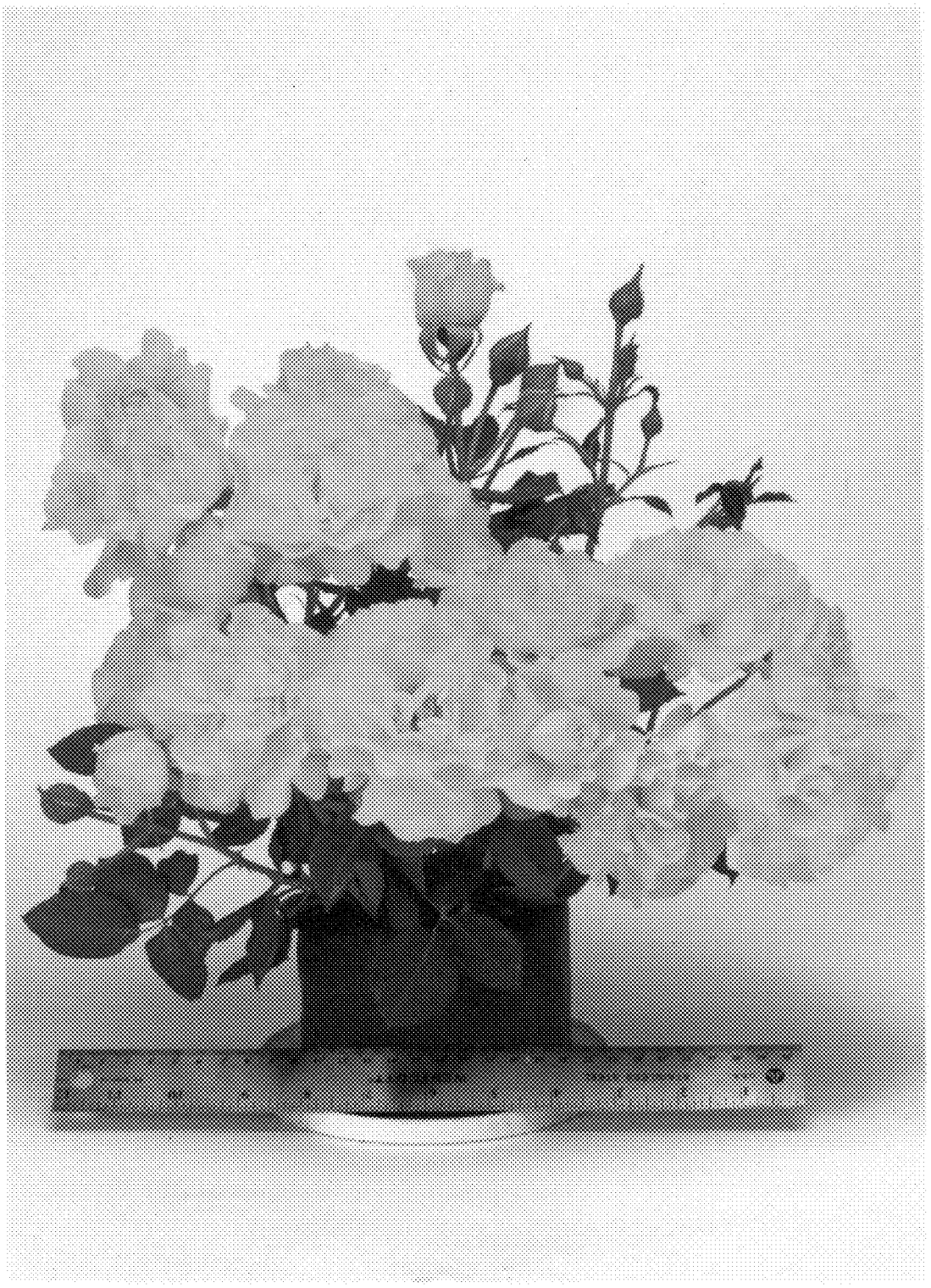

* * * * *